United States Patent
Kwok et al.

(10) Patent No.: US 6,927,859 B2
(45) Date of Patent: Aug. 9, 2005

(54) MICRODENSITOMETER SYSTEM WITH MICROMETER RESOLUTION FOR READING RADIOCHROMIC FILMS

(75) Inventors: Cheuk Sang Kwok, Kowloon (HK); Kit Yee Lee, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

(21) Appl. No.: 10/429,241

(22) Filed: May 5, 2003

(65) Prior Publication Data

US 2004/0008347 A1 Jan. 15, 2004

Related U.S. Application Data

(63) Continuation-in-part of application No. 09/800,962, filed on Mar. 8, 2001, now abandoned.

(51) Int. Cl.[7] .......................... G01N 21/00; G01N 21/86
(52) U.S. Cl. ................................. 356/443; 250/559.02
(58) Field of Search ................................ 356/300, 331, 356/432, 443–445, 326, 328, 332, 334, 404, 434; 378/50, 51; 250/548, 559.01, 559.02, 559.04, 559.05, 559.06, 559.07, 559.08, 559.1

(56) References Cited

U.S. PATENT DOCUMENTS

| | | | |
|---|---|---|---|
| 3,744,916 A | * 7/1973 | Bey et al. .................... 356/632 |
| 3,802,784 A | 4/1974 | Reynolds et al. |
| 3,813,145 A | * 5/1974 | Hedman et al. ............... 349/33 |
| 3,929,553 A | * 12/1975 | van Kempen ............... 156/391 |
| 4,150,899 A | 4/1979 | Nakamura |
| 4,181,436 A | 1/1980 | Wasmund et al. |
| 4,273,419 A | 6/1981 | Geary |
| 4,457,010 A | * 6/1984 | Jenkins et al. .............. 378/167 |
| 4,632,549 A | 12/1986 | Czabaffy et al. |
| 4,674,883 A | 6/1987 | Baurschmidt |
| 4,734,578 A | * 3/1988 | Horikawa .................... 250/234 |
| 4,844,617 A | 7/1989 | Kelderman et al. |
| 5,053,629 A | 10/1991 | Thompson |
| 5,059,764 A | 10/1991 | Baer |
| 5,112,125 A | 5/1992 | Neumann |
| 5,153,926 A | 10/1992 | Jansson et al. |
| 5,255,069 A | 10/1993 | Duarte |
| 5,568,192 A | 10/1996 | Hannah |
| 5,617,213 A | 4/1997 | Shih |
| 5,623,139 A | 4/1997 | Sliski |
| 5,653,539 A | 8/1997 | Rosengaus |
| 5,859,700 A | * 1/1999 | Yang .......................... 356/300 |
| 5,875,022 A | 2/1999 | Kajiwara |
| 5,918,469 A | 7/1999 | Cardella |
| 6,455,860 B1 | 9/2002 | Mooney |
| 2001/0012135 A1 | * 8/2001 | Kurosawa .................... 358/487 |

FOREIGN PATENT DOCUMENTS

JP  63058127 A  * 3/1988  .......... G01N/21/27

* cited by examiner

Primary Examiner—Gregory J. Toatley, Jr.
Assistant Examiner—Gordon J. Stock, Jr.
(74) Attorney, Agent, or Firm—Leydig, Voit & Mayer, Ltd.

(57) ABSTRACT

Radiation dose deposited on a radiochromic film is considered as a dose image. A precise image extraction system with commensurate capabilities is required to measure the transmittance of the dose image and correlate it with radiation dose. The disclosed microdensitometer system is designed to achieve this goal according to the unique characteristics of the radiochromic films, namely (a) the linearity and sensitivity of the dose response of the radiochromic films being highly dependent on the wavelength of the analyzing light and (b) the inherently high spatial resolution of the radiochromic films. The disclosed microdensitometer system consists of a monochromator which provides analyzing light of variable wavelength, a film holder on a high-precision scanning stage, a CCD-dedicated microscope in conjunction with a thermoelectrically cooled CCD camera, corresponding computer interfaces and a microcomputer.

6 Claims, 6 Drawing Sheets

MICRODENSITOMETER SYSTEM WITH MICROMETER RESOLUTION FOR READING RADIOCHROMIC FILMS

This disclosure is a continuation-in-part of U.S. patent application Ser. No. 09/800,962 filed Mar. 8, 2001 now abandoned the content of which is incorporated herein by reference.

FIELD OF THE INVENTION

The invention relates to a microdensitometer system capable of reading radiochromic films with micrometer resolution. Specifically, the invention relates to a system for measuring the transmittance of radiochromic films and correlating the transmittance with the radiation dose imparted on the films.

BACKGROUND OF THE INVENTION

The ultimate aim of radiation treatment is to deliver a prescribed dose to a well-delineated tumour volume and, at the same time, minimize the radiation dose to the surrounding normal tissues. Verification of the three-dimensional dose distribution around the tumour before treatment is given to a patient is essential to ensure the above aim is achieved. A phantom incorporated with a dose-recording medium is usually used as a surrogate for the patient's treatment for verification.

Of all the dose-recording media used, radiocbromic films are gaining popularity in dose verification work owing to their advantages over the conventional media. Radiochromic films are films which change from colorless to a bluish color upon irradiation by ionizing irradiation. The darkness of the blue shade is proportional to the amount of energy deposited on the films. They are insensitive to daylight. There exist two absorption peaks for the exposed films at which the most sensitive measurements can be made. Radiocbromic films are self-developing, tissue equivalent; their responses are practically energy and dose-rate independent. They can offer an extremely fine spatial resolution up to 1200 lines/mm due to their grainless nature. In conclusion, radiochromic films are increasingly being used for measuring two-dimensional dose distribution. This is particularly true in intravascular brachytherapy where detailed dosimetry data at 2–5 mm from the source axis is required for prescribing the radiation dose to a patient.

Radiochromic films need to be read out before any quantitative analysis of the absorbed dose distribution can be made. Currently available two-dimensional densitometers are not primarily designed for reading radiochromic films. There are three major problems associated with those densitometers.

Firstly, they utilise light sources including lasers, fluorescent lamps and light-emitting diodes that do not have an emission spectrum that matches the absorption spectrum of the radiochromic films. This may compromise the sensitivity of the measurement.

Secondly, the wavelength of the light source is not changeable. Transmittance measurement taken at a single wavelength suffers from the disadvantages that measuring at the major absorbing peak may saturate at high-doses whereas measuring at the minor absorbing peak may not be sensitive enough to detect low doses.

Thirdly, those densitometers can only provide a spatial resolution of less than 20 lines/mm due to the size of the light source and photodetection method used. Their low spatial resolution is much inferior to the inherent spatial resolution of 1200 lines/mm of the radiochromic films. Those densitometers therefore fail to satisfy the need for measuring dose distributions in micrometer spatial resolution.

SUMMARY OF THE INVENTION

An object of the present invention is to provide a microdensitometer system which can supply a light source the wavelength of which is changeable and matched to the desired absorption peaks of the radiochromic films for transmittance measurement.

Another object of the invention is to provide a microdensitometer system capable of analysing images with micrometer resolution by using a CCD-dedicated microscope in conjunction with a digital CCD camera.

A further object of the present invention is to provide a microdensitometer system that can display the two-dimensional dose distribution recorded on a radiochromic film.

DISCLOSURE THE INVENTION

There is disclosed herein a microdensitometer system capable of micrometer resolution for reading radiochromic films, comprising:

a film holder for supporting a radio chromic film sample;

a high-precision scanning stage including a monochromatic light source for illuminating the film sample;

a CCD microscope camera for a photographing light from the light source that is transmitted through the film sample; and a microcomputer for analysing data relayed from the CCD microscope camera;

whereby the film sample is translated by the scanning stage to enable analysis of the whole film sample.

Preferably the monochromatic light source is adjustable so as to emit light of a wavelength selected to match precisely the wavelength of an absorption peak of the film sample.

Preferably the monochromatic light source includes an AC voltage regulated monochromator, a coupling fibre optic cable and a collimating lens.

Preferably the film holder includes an open area for illumination of the film sample and a plurality of movable rails for anchoring the film sample.

Preferably the film holder includes two raised borders at opposite corners for spatial indexing of the film sample.

Preferably the film holder includes two receptacles for spatial calibration reticules.

Preferably the film holder includes a further six receptacles for small radio chromic film samples for dose-transmittance calibration.

Preferably two-dimensional dose distribution of the dose image recorded on the radiochromic film sample is displayed on a monitor.

BRIEF DESCRIPTION OF THE DRAWINGS

A preferred form of the invention will now be described by way of example with reference to the accompanying drawings, wherein.

DESCRIPTION OF THE PREFERRED EMBODIMENT

Figure 1:
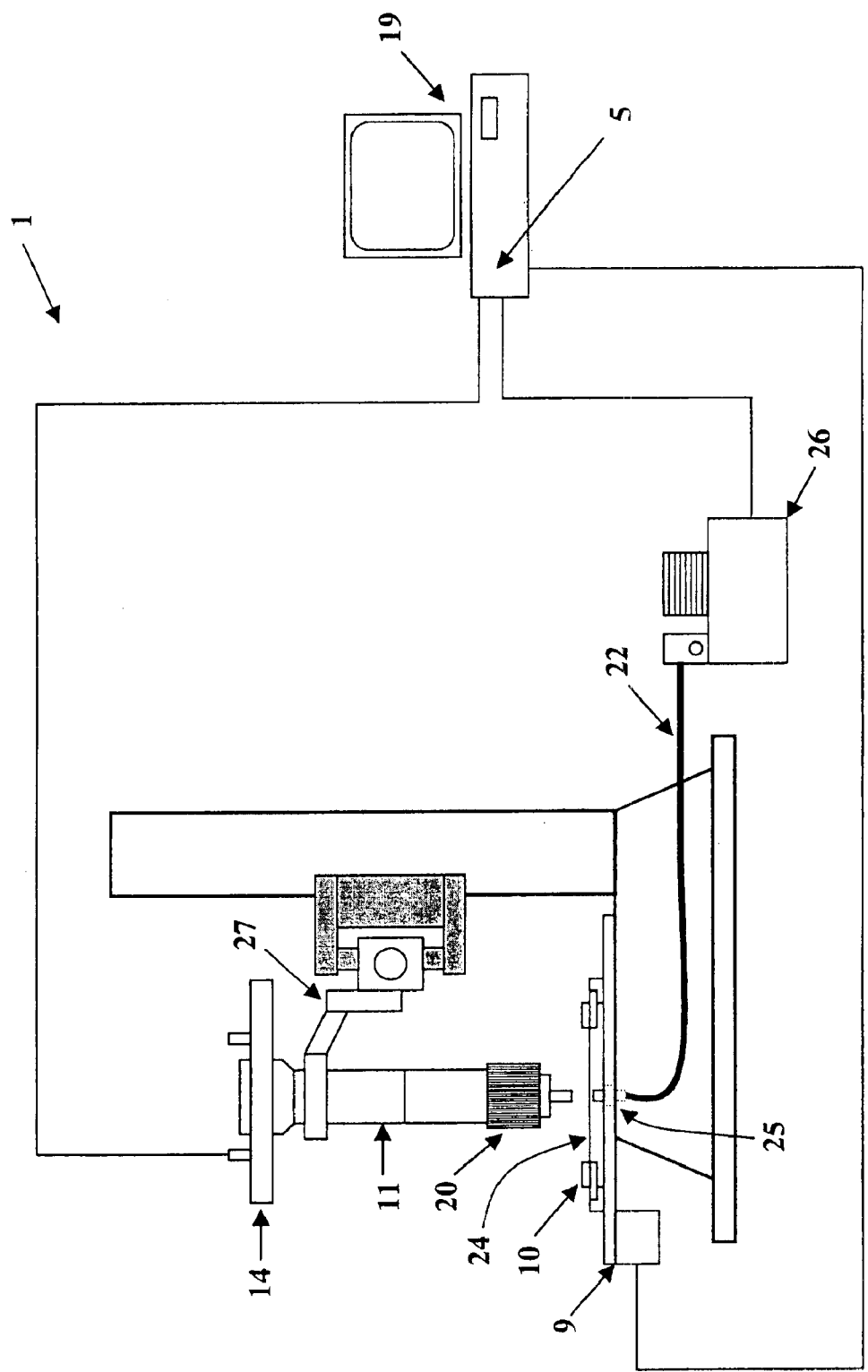
FIG. 1 is a schematic view of a microdensitometer system.

Referring to FIG. 1, the microdensitometer system of the present invention is illustrated.

Microdensitometer system 1 includes a monochromator 26, a film holder 10 on a high precision scanning stage 9, a CCD-dedicated microscope 11, a cooled CCD camera 14, computer interfaces 5 and a microcomputer 19. The monochromatic light output from the monochromator 26 is coupled to a collimating lens 25 via a fibre optic cable 22. The collimating lens 25 is used to convert the divergent beam of light from the fibre optic cable 22 into a parallel beam which trans-illuminates the radiochromic film sample 24 mounted on the film holder 10 from the scanning stage 9 underneath. The magnification and focusing of the film sample is adjusted coarsely by the focusing mount 27 and fine adjustment is done by the focus control 20 of the microscope. The monochromator 26, the scanning stage 9 and the CCD camera 14 are interfaced to and controlled by the microcomputer 19 via software developed in the present invention.

Figure 2:
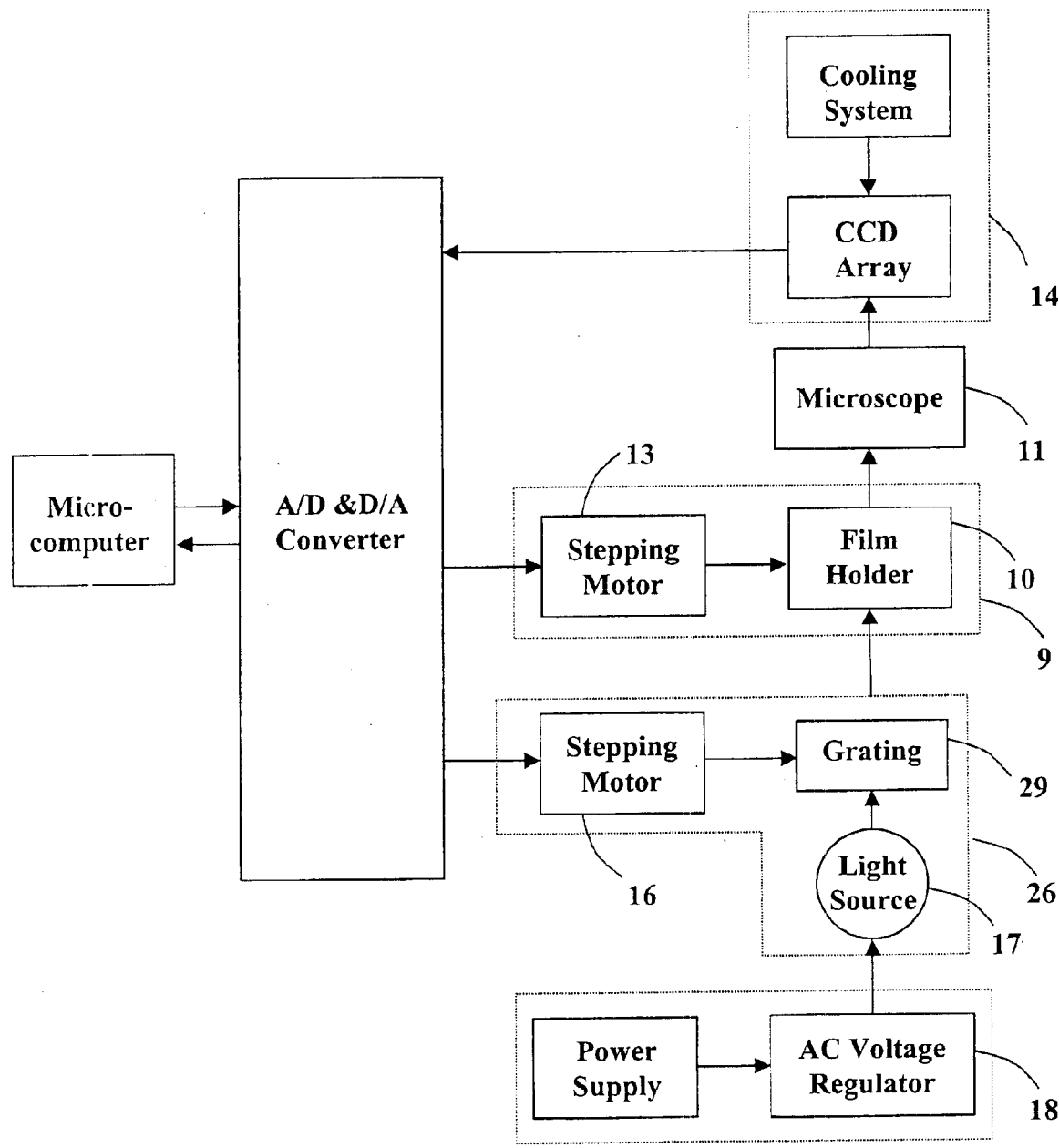
FIG. 2 is a block diagram of the microdensitometer system showing the layout of various components.
Figure 3:
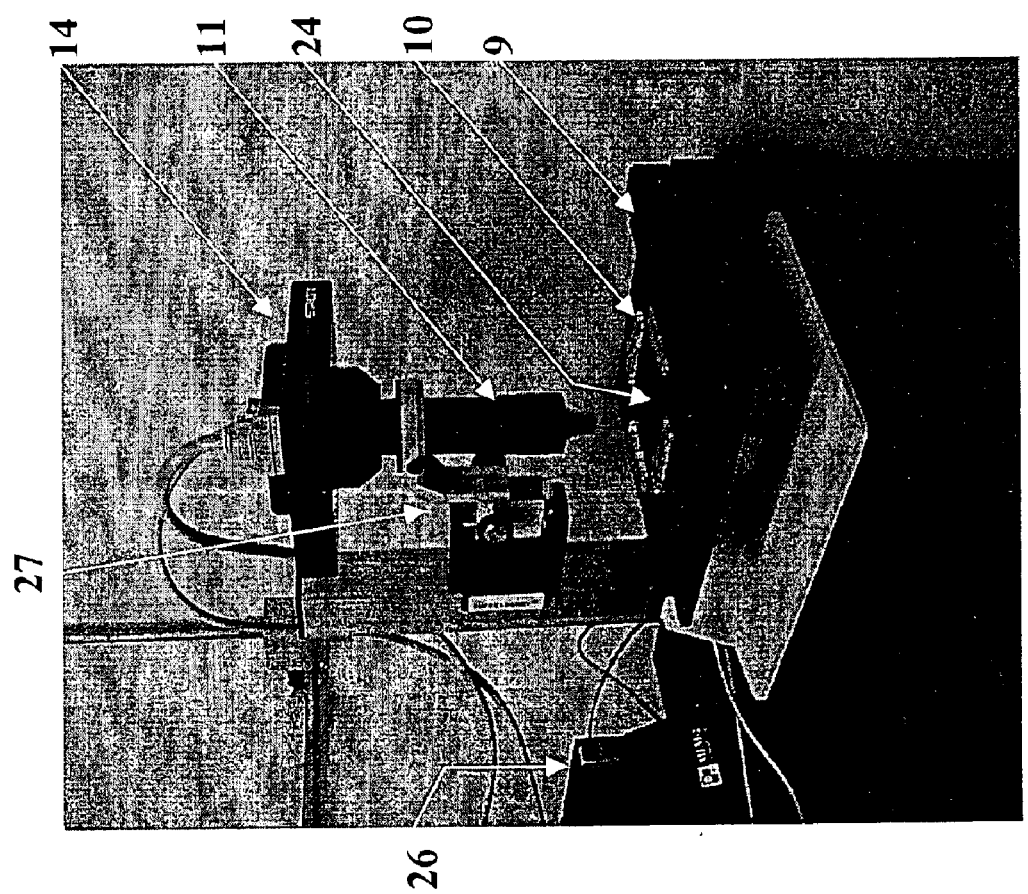
FIG. 3 is a photograph of the microdensitometer part of the system.

Referring to FIG. 2, the white light source 17 used in the monochromator 26 is stabilised by an AC voltage regulator 18 in order to provide a stable output for transmittance measurement. The preferred monochromator 26 is an in-line Fastie-Ebert monochromator with wavelength ranging from 300–800 nm with a readability of ±0.2 nm and an accuracy of ±0.6 nm. The angle of the grating 29 used in the monochromator 26 is controlled by a stepping motor 16. The preferred scanning stage 9 is a high-precision motorised X, Y stage (model no. 6600BS) that offers 6"×6" travel in the respective directions supplied by Conix Research Inc. (Springfield, Oreg.). The X, Y motion is controlled by a stepping motor 13. The X, Y axis accuracy and resolution are 0.1 $\mu$m and 0.05 $\mu$m respectively. The X, Y axis repeatability is better than 1 $\mu$m. The glass support plate of the stage is removed to avoid interference fringe artifacts otherwise caused by the multiple reflections between the glass plate and scanned film surface. Instead, an open film holder 10 that can be secured on the scanning stage 9 for scanning was fabricated. Light transmitted through the film sample is collected by the CCD-dedicated microscope 11 and imaged by the cooled CCD camera 14. A photograph of the microdensitometer is shown in FIG. 3.

In this preferred embodiment, the microscope used was a CCD-dedicated microscope 11 (Infinivar™ microscope) manufactured by Infinity Photo-Optical Company (Boulder, Colo.). It has a C-mount to which a CCD camera can be attached. It can focus continuously without blackout from infinity to 9 mm by a half-twist of its focus control 20. This microscope has no objective lens changes and does not require any additional optics to operate throughout its 40:1 range, which facilitates routine operation. In order to enable making measurements at low transmittance, a focal compressor was incorporated to reduce the optical and mechanical tubelength and enhance the light efficiency at the expense of magnification power.

Yet the effective magnification, based on this ½" format CCD camera and 15" monitor, still ranges from 190× to 34× corresponding to a field of view of 1.6 to 8.5 mm and it is considered to be adequate for the present application.

Again in this preferred embodiment, the CCD camera 14 selected was a scientific-grade low noise camera (SPOT™ JR) supplied by Diagnostic Instruments, Inc. (Michigan, N. Dak.). It is a full frame camera that employs a mechanical shutter to control the exposure time and to block the light during charge transfer and readout. The chip used is a grade 2 Kodak KAF 0400 CCD (Rochester, N.Y.). It is a chip of ½" format with an array of 768×512 pixels each of size 9 $\mu$m×9 $\mu$m. The pixel size matches the typical resolution of the microscope. This gives an imaging area of 6.9×4.6 mm$^2$. The full-well capacity is 85,000 electrons. The CCD camera is cooled by a thermoelectric cooler with forced air to a temperature of 37 degrees below ambient temperature, that is to −17° C. at a typical laboratory temperature of 20° C., thus making the dark current at about 0.2 electron/pixel/second. The spectral quantum efficiency is about 40% for the range of 660–700 nm, highest amongst other wavelengths. This makes the CCD ideally suited for measuring the absorption of the radiochromic films.

The camera 14 digitises each pixel as it comes off the CCD chip in the camera head. This will give an image of perfect registration of the pixels and minimal noise. The pixel depth used is 12-bit for the present application of which a 4096 grey-scale is considered to be adequate.

Figure 4B:
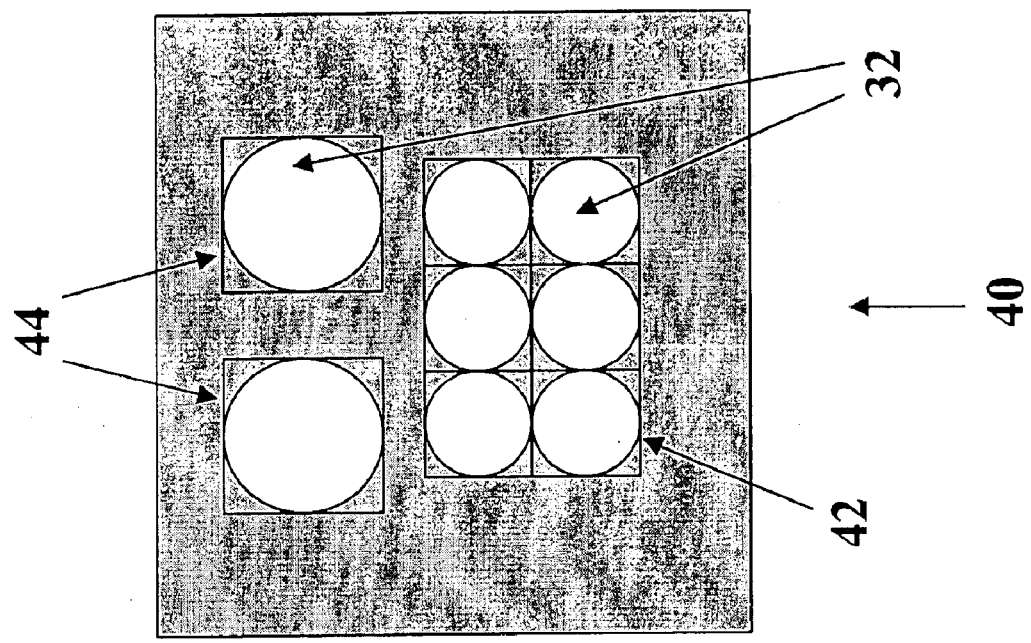
FIG. 4B is a schematic view of a film holder for mounting calibration films and reticules used for dose calibration and spatial calibration respectively.
Figure 4A:
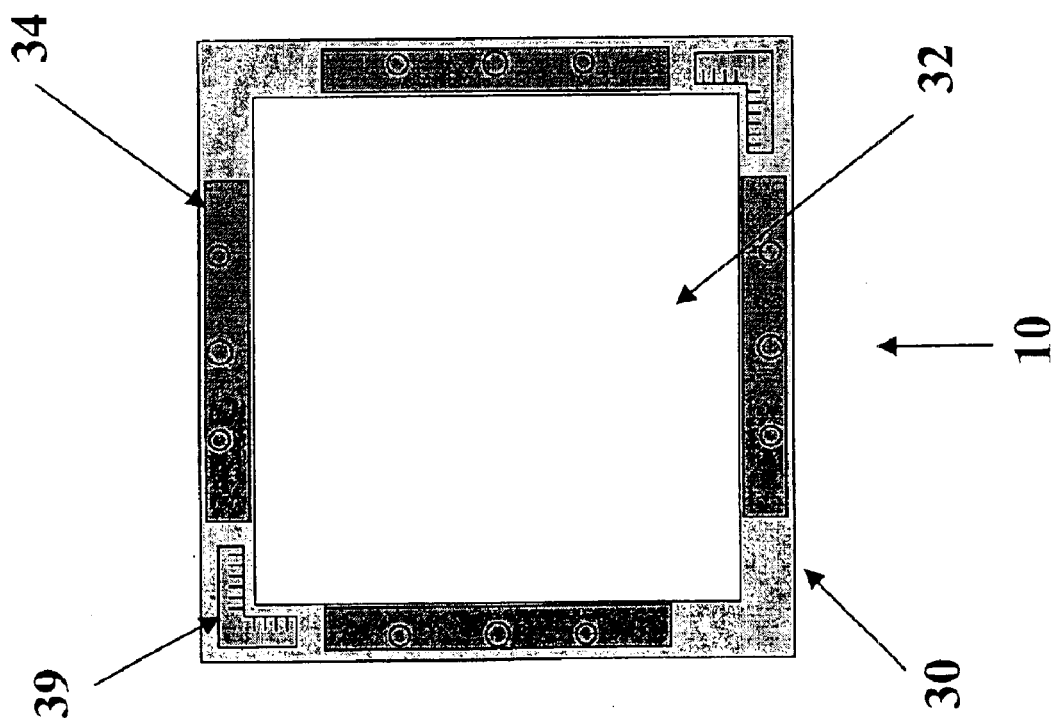
FIG. 4A is a schematic view of the film holder for mounting a film sample.

In FIG. 4A, the film holder 10 is shown schematically. Its frame 30 is made of aluminium with an open area of 11.7×11.7 cm$^2$. The film is securely clamped without bulging by movable rails 34 fixed by the guide pins 36 and fixation screws 38 at the four edges of the holder. The holder also has raised border 39 at two opposing corners that the scanned film can be pushed against to provide spatial indexing for the film. This feature is particularly useful for reproducible film positioning needed for repeated scans when a double exposure technique or film registration is used. Films with dimensions smaller than 12.5 cm×12.5 cm can be mounted on a larger paper frame before securing to the holder. Another film holder 40 shown schematically in FIG. 4B was also fabricated. This can accommodate 2 reticles in the receptacles 44 and 6 pieces of calibration film measuring 2×2 cm$^2$ in the receptacles 42 for spatial and transmittance calibration, respectively. Both receptacles have an open area 32 through which the analysing light passes.

Principle of Obtaining Micrometer Resolution

Figure 5:
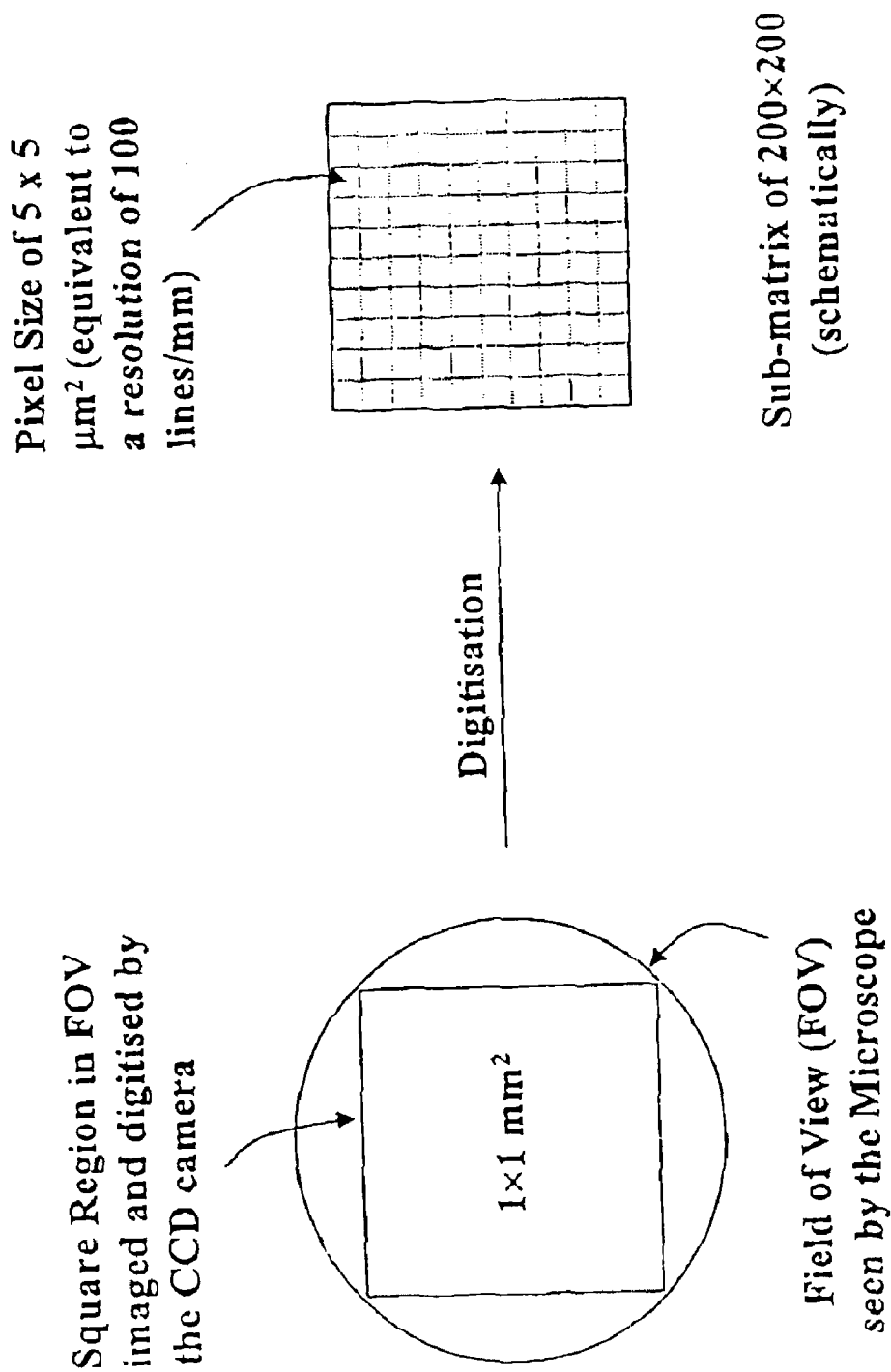
FIG. 5 is a schematic diagram showing how micrometer resolution can be accomplished by the present invention.

The capability of the disclosed microdensitometer system in providing micrometer resolution relies on the magnification provided by the microscope in conjunction with the acquisition and simultaneous digitisation of the image by the CCD camera. The principle is illustrated schematically in FIG. 5. Typically an area of 1 mm×1 mm is included in the field of view (FOV) of the microscope. The image formed is acquired and digitised by the CCD camera into a matrix of typically 200×200 pixels. Thus a pixel size of 5 $\mu$m×5 $\mu$m which is equivalent to 100 lines/mm can be accomplished.

The overall resolution is primarily determined by the magnification offered by the microscope and the size of the matrix used in digitisation. Essentially, each pixel in the matrix acts as an individual micro-detector for the transmittance measurement of the area to be investigated.

Operation

Figure 6:
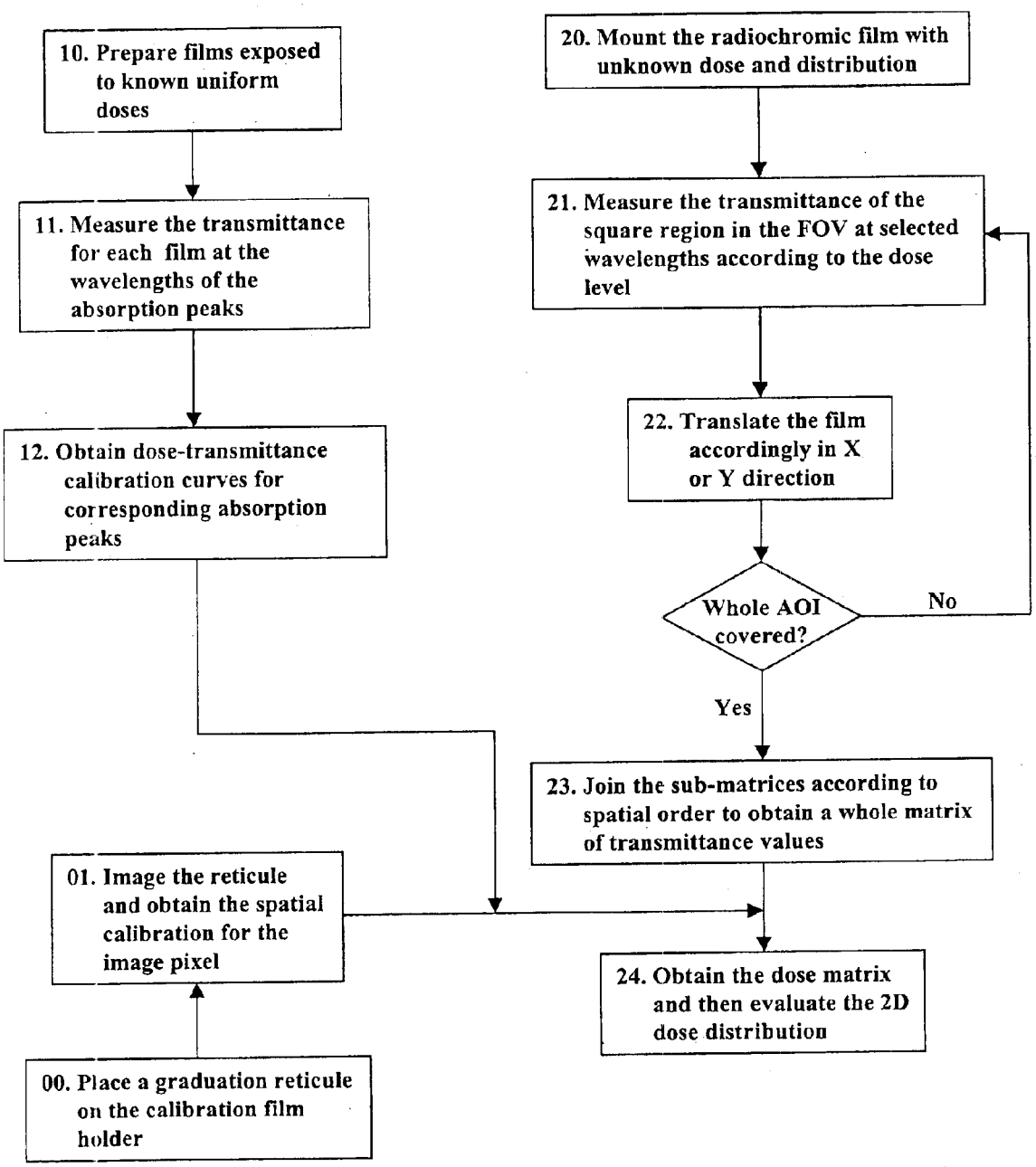
FIG. 6 is a block diagram explaining the steps in acquiring a two-dimensional dose distribution recorded on a radiochromic film.

The acquisition of the two-dimensional dose distribution recorded on a radiochromic film is now described with reference to the operational steps in FIG. 6. Before any quantitative analysis can be made, spatial calibration for the image pixels (steps 00, 01) and calibration of the transmittance versus known radiation doses at wavelengths of the absorption peaks (steps 10, 11, 12) need to be established. The spatial calibration factor and dose calibration curves for the designated wavelengths are then stored in the microcomputer for later retrieval.

In step 20, a radiochromic film with an unknown dose distribution is mounted on the film holder and placed on the high-precision scanning stage. The transmittance of the square region included in the FOV of the microscope is measured initially with a range of wavelength from 600–750 nm. Transmittance images at the wavelengths corresponding to the two absorption peaks are then recorded, digitised by the CCD camera, and stored as two separate sub-matrices in the microcomputer for later processing.

For each of the two wavelengths, the transmittance measurement is performed several times and the average value is taken to reduce random noise. All other corrections such as dark frame and bias frame corrections which are known to the trade of using CCD as a detector are applied (step 21).

Once the measurement of the square region is accomplished, the film is stepped by the scanning stage (step 22) in X or Y direction such that the next square region is adjacent to the previous one and the step 21 is repeated. It should be noted that the range of wavelength between the two previously selected wavelengths may be run for the new 1 mm×1 mm area.

A possible change in the wavelengths corresponding to the absorption peaks for the second region is noted. This measure-and-step procedure is repeated until the whole area of interest (AOI) is covered. In step 23, all the sub-matrices are joined according to the spatial order of their corresponding regions to form a matrix of the transmittance values of the whole AOI for each of the two absorption peaks. Finally in step 24, the transmittance matrices are then transformed into a dose matrix through the corresponding calibration curves. The contouring of the dose values in the AOI will be output in the form of a two-dimensional dose distribution that can then be compared readily to the prescribed dose distribution for the patient.

All measurements are made in a light-tight enclosure which houses the microdensitometer system in order to eliminate any stray light from entering the CCD camera during image acquisition. All the image and matrix manipulation in the steps 23–24 are done by software developed using the Matlab (MathWorks, Inc., Natick, Mass.).

The foregoing application of this invention is not restricted to radiochromic films. It is readily obvious to one skilled in the art to use the present invention to read any kind of dye films of which the transmittances are spectral dependent. Such films include pressure films used in mechanical and biomechanical tests.

What is claimed is:

1. A microdensitometer system for reading radiochromic films, comprising:
   a monochromatic light source producing monochromatic light at a wavelength that can be varied;
   a film holder for scanning a radiochromic film sample illuminated by monochromatic light from the monochromatic light source;
   a scanning stage translating the film holder for scanning all of the radiochromic film sample with the monochromatic light;
   a microscope collecting light from the monochromatic light source and transmitted through the radiochromic film sample;
   a cooled charge coupled device (CCD) camera mounted on the microscope and forming an image from the light collected by the microscope; and
   a microcomputer for processing the image that is produced by the cooled CCD camera.

2. The microdensitometer system according to claim 1, wherein the monochromatic light source is adjustable in wavelength to emit light of a wavelength selected to match wavelength of peak absorption of the film sample.

3. The microdensitometer system according to claim 1, wherein the film holder includes two receptacles for spatial calibration reticles.

4. The microdensitometer system according to claim 1, wherein the film holder includes six receptacles for radiochromic film samples for dose-transmittance calibration.

5. A microdensitometer system for reading radiochromic films, comprising:
   a monochromatic light source producing monochromatic light at a wavelength that can be varied;
   a film holder for scanning a radiochromic film sample illuminated by monochromatic light from the monochromatic light source, wherein the film holder includes an open area for illumination of the film sample and a plurality of screw clamps for anchoring the film sample;
   a scanning stage translating the film holder for scanning all of the radiochromic film sample with the monochromatic light;
   a microscope collecting light from the monochromatic light source and transmitted through the radiochromic film sample:
   a cooled charge coupled device (CCD) camera mounted on the microscope and forming an image from the light collected by the microscope; and
   a microcomputer for processing the image that is produced by the cooled CCD camera.

6. A microdensitometer system for reading radiochromic films, comprising:
   a monochromatic light source producing monochromatic light at a wavelength that can be varied;
   a film holder for scanning a radiochromic film sample illuminated by monochromatic light from the monochromatic light source, wherein the film holder includes two raised borders at opposite corners for spatial indexing of the film sample;
   a scanning stage translating the film holder for scanning all of the radiochromic film sample with the monochromatic light;
   a microscope collecting light from the monochromatic light source and transmitted through the radiochromic film sample;
   a cooled charge coupled device (CCD) camera mounted on the microscope and forming an image from the light collected by the microscope; and
   a microcomputer for processing the image that is produced by the cooled CCD camera.

* * * * *